US009023596B2

(12) United States Patent
Weber et al.

(10) Patent No.: US 9,023,596 B2
(45) Date of Patent: May 5, 2015

(54) RECOMBINANT POKEWEED ANTIVIRAL PROTEINS, COMPOSITIONS AND METHODS RELATED THERETO

(71) Applicants: Cedus, Inc., Fort Collins, CO (US); Colorado State University Research Foundation, Fort Collins, CO (US)

(72) Inventors: Eric R. Weber, Fort Collins, CO (US); Torrance M. Nett, Bellvue, CO (US)

(73) Assignees: Colorado State University Research Foundation, Fort Collins, CO (US); Cedus, Inc., Fort Collins, CO (US)

( * ) Notice: Subject to any disclaimer, the term of this patent is extended or adjusted under 35 U.S.C. 154(b) by 0 days.

(21) Appl. No.: 14/045,437

(22) Filed: Oct. 3, 2013

(65) Prior Publication Data

US 2014/0094592 A1 Apr. 3, 2014

Related U.S. Application Data

(62) Division of application No. 13/054,187, filed as application No. PCT/US2009/050685 on Jul. 15, 2009, now Pat. No. 8,575,109.

(60) Provisional application No. 61/080,773, filed on Jul. 15, 2008.

(51) Int. Cl.
*A61K 38/00* (2006.01)
*C07K 14/415* (2006.01)
*C07K 7/23* (2006.01)

(52) U.S. Cl.
CPC ............... *C07K 14/415* (2013.01); *A61K 38/00* (2013.01); *C07K 7/23* (2013.01); *C07K 2319/33* (2013.01); *C07K 2319/55* (2013.01)

(58) Field of Classification Search
None
See application file for complete search history.

(56) References Cited

U.S. PATENT DOCUMENTS

| | | | | |
|---|---|---|---|---|
| 8,575,109 | B2 | 11/2013 | Weber | |
| 2005/0277582 | A1 | 12/2005 | Nett et al. | |
| 2007/0141548 | A1 * | 6/2007 | Kohl et al. | 435/1.1 |

FOREIGN PATENT DOCUMENTS

| | | |
|---|---|---|
| WO | 9009799 | 9/1990 |

OTHER PUBLICATIONS

Heuer et al., Development of a Sensitive Peptide-Based Immunoassay: Application to Detection of the Jun and Fos Oncoproteins; Biochemistry, vol. 35, pp. 9069-9075, 1996.*

Yang et al., Cytotoxic Activity of Gonadotropin-Releasing Hormone (GnRH)-Pokeweed Antiviral Protein Conjugates in Cell Lines Expressing GnRH Receptors; Endocrinology, vol. 144, No. 4, 1456-1463, 2003.*

Rajamohan et al., High-Level Expression and Purification of Biologically Active Recombinant Pokeweed Antiviral Protein; Protein Expression and Purification, vol. 16, pp. 359-368, 1999.*

Erlanson et al., The leucine zipper domain controls the orientation of AP-1 in the NFAT-AP-1-DNA complex; Chemistry & Biology, vol. 3, pp. 981-991, 1996.*

Fujiwara, K. et al. "Sandwich Enzyme Immunoassay of Tumor-Associated Antigen Sialosylated Lewisx using Beta-D-Galactosidase Coupled to a Monoclonal Antibody of IgM Isotype." J. Immunol. Methods, 112:77-83 (1988).

Japanese Patent Office. First Official Action in the prosecution of Japanese Patent Application No. 2011-518880, dated Feb. 28, 2014.

Ramakrishnan, S. and Houston, L.L. "Comparison of the Selective Cytotoxic Effects of Immunotoxins Containtint Ricin A Chain or Pokeweed Antiviral Protein and Anti-Thy 1.1 Monoclonal Antibodies." Cancer Res., 44:201-208 (1984).

Honjo E., and Watanabe, K. "Expression of Mature Pokeweed Antiviral Protein with or without C-terminal Extrapeptide in *Escherichia coli* as a fusion with Maltose-Binding Protein." Biosci. Biotechnol. Biochem., 63(7), 1291-1294 (1999).

Anonymous, "BL21-Al One-Shot, Chemically Competent *E. coli*," Retrieved from the web on Nov. 26, 2012, <http://tools.invitrogen.com/content/sfs/manuals/oneshot_bl21ai_man.pdf>, pp. 1-20.

Anonymous, "Instructions GMBS and Sulfo-GMBS" Retrieived from web on Nov. 26, 2012, <http://www.piercenet.com/instructions/2161763.pdf>, pp. 1-3.

Chaddock, J. et al., "Pokeweed Antiviral Protein (PAP) Mutations Which Permit *E. coli* Growth Do Not Eliminate Catalytic Activity Towards Prokaryotic Ribosomes," Nucleic Acids Research, 1994, pp. 1536-1540, vol. 22, No. 9.

Dore, J. et al., "Mutations Dissociating the Inhibitory Activity of the Pokeweed Antiviral Protein on Eukaryote Translation and *Escherichia coli* Growth," Nucleic Acids Research, Sep. 1993, pp. 4200-4205, vol. 21, No. 18.

Qi, L. et al., "Binding and Cytotoxicity of Conjugated and Recombinant Fusion Proteins Targeted to the Gonadotropin-Releasing Hormone Receptor," Cancer Research, Mar. 2004, pp. 2090-2095, vol. 64 No. 6.

Saida, F., "Unit 5.19 Overview on the Expression of Toxic Gene Products in *Escherichia coli*," Current Protocols in Protein Science, Nov. 2007, pp. 5.19.1-5.19.13, vol. Supplement, No. 50.

* cited by examiner

*Primary Examiner* — Jennifer Dunston
*Assistant Examiner* — Addison D Ault
(74) *Attorney, Agent, or Firm* — MacMillan, Sobanski & Todd, LLC

(57) ABSTRACT

The present invention provides novel, modified pokeweed antiviral proteins, nucleic acids that encode the proteins, conjugates that incorporate the proteins, and methods to make and use the proteins. The present invention also provides methods to administer the conjugates to animals, for the purpose of directing toxin to particular cells.

7 Claims, 11 Drawing Sheets

ATGTGCGGAGGCGGAGGCAGTGTGAATACAATCATCTACAATGTTGGAAG
TACCACCATTAGCAAATACGCCACTTTTCTGAATGATCTTCGTAATGAAG
CGAAGATCCAAGTTAAATGCTATGGAATACCAATGCTGCCAATACA
AATACACACTAATCCAAAGTACGTGTTGGTTGAGCTCCAAGGTCAAATAAAAA
AACCATCACACTAATGCTGAGACGAAACAATTTGTATGTGGTTATT
CTGATCCCTTTGAAACCAATAAATGTCGTTACCATATCTTTAATGATATC
TCAGTACTGAACGCCAAGATGTAGAGACTACTCTTTGCCCAAATGCCAA
TTCTCGTGTTAGTAAAAACATAAACTTTGATAGTCAGTCCAACATTGG
AATCAAAAGCGGGAGTAAATATTCAAGAAGTCAGGGAATTCAA
ATACTCGACAGTAATTCCTATTGGTAGCCATAAATGGTATCCAGAGG
GAAACCGAAGCAAGATTCAAGACATAGAGAATCAGGTGAAACTAATTTTAACAGA
CAGCAAGATTCAAGACATAGAGAATCAGGTGAAACTAATTTTAACAGA
GCATTCAACCCTAATCCAAAGTACTTAATTTGCAAGAGACATGGGTAA
GATTTCAACAGCCTGATGCCAGTGGTGCCAAGAATGGATAGTGTTGAGAGTGGAT
TCGAGCTAGTGGATGTAGCCTGATGTAGCACTCTTAAACTACGTTGGTGGAGCTGTCA
GAAATCAAGCCTGATGTAGCACTCTTAAACTACGTTGGTGGGAGCTGTCA
GACAACTT**TATAACCAAAATGCCATGTTTCCTCAACTTATAATGTCTACTT
ATTATAATTACATGGTTAATCTTGGTGATTCTATTTGAAGGATTC(TGA)**

FIG. 7

MCGGGGSVNTIIYNVGSTTISKYATFLNDLRNE
AKDPSLKCYGIPMLPNTNTNPKYVLVELQGSN
KKTITLMLRRNNLYVMGYSDPFETNKCRYHIFN
DISGTERQDVETTLCPNANSRVSKNINFDSRY
PTLESKAGVKSRSQVQLGIQILDSNIGKISGVM
SFTEKTEAEFLLVAIQMVSEAARFKYIENQVKT
NFNRAFNPNPKVLNLQETWGKISTAIHDAKNG
VLPKPLELVDASGAKWIVLRVDEIKPDVALLNY
VGGSCQT<u>TYNQNAMFPQLIMSTYYNYVNLGD
LFEGF</u>

MCGGGGSVNTIIYNVGSTTISKYATFLNDLRNEAKDPSLKCYGIPMLPNTNTNPK
------VNTIIYNVGSTTISKYATFLNDLRNEAKDPSLKCYGIPMLPNTNTNPK

YVLVELQGSNKKTITLMLRRNNLYVMGYSDPFETNKCRYHIFNDISGTERQDVE
YVLVELQGSNKKTITLMLRRNNLYVMGYSDPFETNKCRYHIFNDISGTERQDVE

TTLCPNANSRVSKNINFDSRYPTLESKAGVKSRSQVQLGIQILDSNIGKISGVMSF
TTLCPNANSRVSKNINFDSRYPTLESKAGVKSRSQVQLGIQILDSNIGKISGVMSF

TEKTEAEFLLVAIQMVSEAARFKYIENQVKTNFNRAFNPNPKVLNLQETWGKIST
TEKTEAEFLLVAIQMVSEAARFKYIENQVKTNFNRAFNPNPKVLNLQETWGKIST

AIHDAKNGVLPKPLELVDASGAKWIVLRVDEIKPDVALLNYVGGSCQTTYNQN
AIHDAKNGVLPKPLELVDASGAKWIVLRVDEIKPDVALLNYVGGSCQTT------

AMFPQLIMSTYNYVNLGDLFEGF

FIG. 10

CGGGGSVNTIIYNVGSTTISKYATFLNDLRNEAKDPSLK
CYGIPMLPNTNTNPKYVLVELQGSNKKTITLMLRRNN
LYVMGYSDPF
ETNKCRYHIFNDISGTERQDVETTLCPNANSRVSKNINF
DSRYPTLESKAGVKSRSQVQLGIQILDSNIGKISGVMSF
TE
KTEAEFLLVAIQMVSEAARFKYIENQVKTNFNRAFNPNPK
VLNLQETWGKISTAIHDAKNGVLPKPLELVDASGAKWI
VL
RVDEIKPDVALLNYVGGSCQTTY<u>NQNAMFPQLIMSTYY</u>
<u>NYVNLGDLFEGF</u>

FIG. 11

RECOMBINANT POKEWEED ANTIVIRAL PROTEINS, COMPOSITIONS AND METHODS RELATED THERETO

RELATED APPLICATIONS

This application is a divisional application of U.S. Patent Application Ser. No. 13/054,187, having a 371 filing date of Mar. 21, 2011, now allowed, which is a national stage application filed under 37 C.F.R. §1.371 of international application PCT/US2009/050685 filed Jul. 15, 2009, which claims priority to U.S. Provisional Application Ser. No. 61/080,773, filed Jul. 15, 2008, the entire disclosures of which are expressly incorporated herein by reference.

SEQUENCE LISTING

The instant application contains a Sequence Listing which has been submitted via EFS-web and is hereby incorporated by reference in its entirety. The ASCII copy, created on Jan. 19, 2011, is named 1-51469.txt and is 13.2 kilobytes in size. The nucleic and amino acid sequences listed in the accompanying sequence listing are shown using standard letter abbreviations for nucleotide bases, and three letter cod for amino acids, as defined in 37 C.F.R. 1.822. Only one strand of each nucleic acid sequence is shown, but the complementary strand is understood as included by any reference to the displayed strand.

TECHNICAL FIELD

This invention relates generally to molecular biology and biochemistry, more particularly related to modified ribosome inactivating proteins from pokeweed plant. The pokeweed plant is also known as *Phytolacca americana* and the pokeweed ribosome inactivating protein is also called pokeweed antiviral protein, often abbreviated "PAP." The invention is also related to medicine, including veterinary medicine.

BACKGROUND OF THE INVENTION

Compound-conjugated pokeweed antiviral protein (PAP) and conjugates of other natural toxins, such as ricin and diphtheria toxin, have long held the promise of therapeutic efficacy. In theory, the presence of a natural ligand as the "compound" portion of the conjugates results in target cell damage, and no other cellular damage. In practice, imprecise targeting results in toxicity, due, in part, to unconjugated toxin causing unintended cellular damage. With regard to PAP, one problem is that conjugated PAP and unconjugated PAP are so similar in size that separation techniques can not distinguish between them.

Natural (also referred to as "native") PAP is isolated from the pokeweed plant, and while attempts have been made to utilize natural PAP in a compound-toxin conjugate, such attempts have not proved reliable. As would be expected, variability in isoforms, from year to year and batch to batch, proved onerous and unworkable in the context of pharmaceutical quality control. Moreover, some isoforms did not conjugate, and different isoforms conjugated differently from each other.

Ideally, recombinant expression would provide control over these variables. Recombinant expression of PAP, however, has also met with difficulty. Previous expression in *E. coli* resulted in toxicity and inhibition of growth, as well as accumulation of recombinant pokeweed antiviral protein (rPAP) in inclusion bodies. In this regard, recombinant PAP required a separate solubilization step and subsequent refolding of the protein, resulting in poor yield and difficult scale-up. Other attempts in *E. coli*, *S. cerevisiae*, plants and *P. pastoris* resulted in low yields, or, in the case of *P. pastoris*, introduction of sequences that could potentially induce an inflammatory response. Moreover, recombinant PAP-compound fusion proteins either failed to bind or direct toxin to the target cells, or showed greatly reduced activity compared to natural PAP.

Therefore, a rPAP molecules having a free cysteine, conjugates made from them, and methods to produce rPAP, especially one that is high yield, results in easily folded and purified rPAP, and optionally provides an rPAP chemically available for conjugation, is a significant contribution.

SUMMARY OF THE INVENTION

In general terms, this invention provides compositions comprising recombinant pokeweed antiviral proteins having a free cysteine, preferably a terminal cysteine, more preferably an N-terminal cysteine. Also provided are those rPAP molecules wherein the PAP is a full length rPAP, more preferably a full length rPAP comprising a free cysteine, most preferably a full length rPAP comprising a free cysteine and an amino acid linker Preferred are those rPAP molecules comprising an N-terminal Cys and an amino acid linker, most preferably those which have at least one repeat of Gly-Gly-Gly-Gly-Ser (SEQ ID NO. 3). More preferred are Cys-Gly-Gly-Gly-Gly-Ser (SEQ ID NO.4)—full length rPAP and Cys-Gly-Gly-Gly-Gly-Ser-Gly-Gly-Gly-Gly-Ser (SEQ ID NO. 5)—full length rPAP.

The present invention provides rPAP which does not kill host cells when expressed according to the present methods. rPAP utilized in the present compositions and methods is preferably equal to or greater than 29.5 Daltons, more preferably equal to or greater than 30 Daltons, most preferably equal to or greater than 30.5 Daltons. However, also within the scope of the present invention are compositions and methods that utilize full length rPAP having a molecular weight equal to or greater than 31.5, 31.75 and 32 Daltons. Full length rPAP proteins (that which equate to the molecular weight of a natural PAP that has not been post-translationally modified) is the preferred material used in the present invention.

Also provided are nucleic acids, plasmids and cells comprising the inventive nucleic acids and proteins, with a preferred cell being *E. coli*.

Also provided are conjugates having the structure:

X-Y-Z, wherein X is full length rPAP having a free cysteine; Y is absent or a chemical linker, and Z is a compound.

Preferred are those compounds which are cell-targeting proteins, more preferably those selected from the group consisting of: an antibody; a hormone; a modified hormone releasing factor; and a hormone releasing factor. Preferred are those compounds wherein the chemical linker is a flexible linker, more preferred are those with a heterobifunctional linker, most preferred are those with a linker having a maleimido group. Preferred are those conjugates as described wherein the linker is selected from the group consisting of: GMBS; EMCS; SMPH; SPDP; and LC-SPDP. Most preferred are those conjugates wherein said linker is GMBS and said protein is d-lys$_6$-gonadotropin releasing hormone.

Also provided are methods to conjugate an rPAP herein with another compound, comprising inducing a chemical bond between said free cysteine of the recombinant pokeweed antiviral protein and another compound. Preferred methods are those as described, wherein said chemical bond is induced via a hetero-bifunctional crosslinker, more preferably those wherein the chemical bond is induced between the free cysteine and a maleimido group on the compound. Most preferred are those wherein the hetero-bifunctional crosslinker is GMBS, and/or the compound is d-lys$_6$-gonadotropin releasing hormone.

Also provided are methods to bind GMBS linker to d-lys6-gonadotropin releasing hormone, comprising incubating GMBS with d-lys6-gonadotropin releasing hormone under non-aqueous conditions, preferably wherein said non-aqueous condition comprises the steps of: solubilizing GMBS in methanol to create a first non-aqueous solution; solubilizing d-lys6-gonadotropin releasing hormone in methanol to create a second non-aqueous solution; mixing said first and second non-aqueous solutions at a molar ratio of 1.1:1.

Also provided are methods to obtain rPAP, comprising expressing a nucleic acid which encodes full length rPAP in *E. coli*.

Also provided are methods to grow cells, comprising: incubating cells transformed with nucleic acid comprising full-length rPAP, wherein the rPAP is under the control of a T7 promoter system, and wherein said T7 promoter system has RNA polymerase under the control of an arabinose promoter. Preferred are those methods wherein said cells are *E. coli* cells. Preferred are those methods wherein the rPAP comprises a free cysteine, most preferred are those wherein the rPAP comprises a terminal cysteine. Also preferred are those methods wherein the full length rPAP is selected from the group consisting of: a chemically-modified rPAP, a natural variant rPAP, and a genetically-engineered rPAP.

Also provided are conjugates comprising the PAP compositions herein. Particularly preferred are those having the structure:

X-Y-Z, wherein X is full length rPAP having N-terminal Cys-Gly-Gly-Gly-Gly-Ser (SEQ ID NO. 4); Y is a chemical linker, and Z is a protein.

Most preferred are those wherein X is GMBS and Z is d-lys6-GnRH.

Definitions

"Free cysteine" means any cysteine other than one which is bound to another cysteine via a di-sulfhydryl bond. In this regard, "free cysteine" includes cysteines that are bound to another residue or compound, so long as the cysteine is not bound to another cysteine via a di-sulfhydryl bond.

"Full length rPAP" means any recombinant PAP which has toxin activity and has a molecular weight greater than or equal to 29,500 Daltons.

These and other features and advantages of this invention will become more apparent to those skilled in the art from the detailed description of a preferred embodiment. The drawings that accompany the detailed description are described below.

BRIEF DESCRIPTION OF THE DRAWINGS

FIG. 7: Nucleic acid of the present invention—rPAP DNA sequence—SEQ ID NO. 10.

FIG. 8: Amino Acid of the present invention—rPAP Protein Sequence—SEQ ID NO. 1. Bold: ATG and linker sequences; Black: Native, mature PAP sequences; Bold and Underlined: Native Pre-PAP sequences that encode the C-terminal portion of the protein that is post-translationally cleaved off in the plant.

Figure 9:
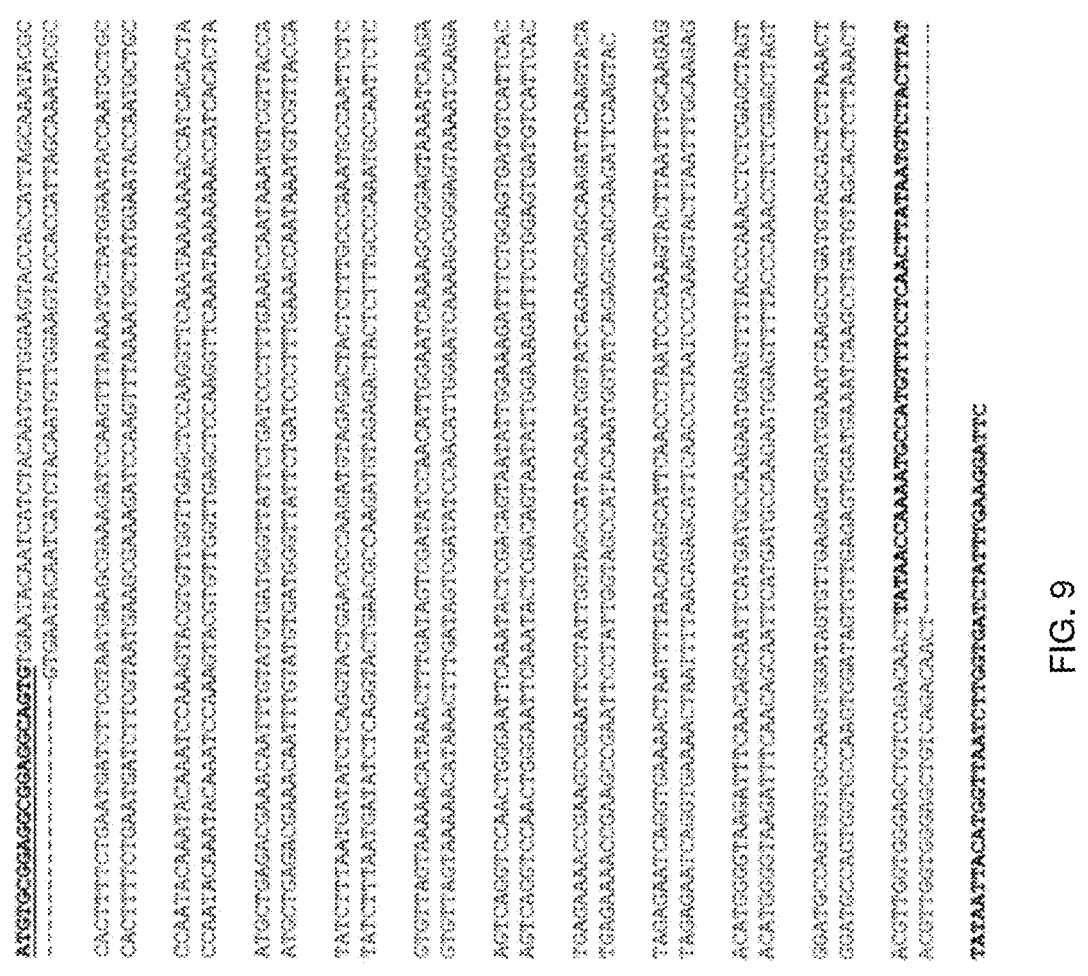

FIG. 9: Alignment of present rPAP (upper)—SEQ ID NO. 2, and native, mature (post translationally-modified in plants) PAP (lower) (SEQ ID NO. 11) expressed DNA sequences.

FIG. 10: Alignment of rPAP (upper) (SEQ ID NO. 1) and native, mature PAP (lower) (SEQ ID NO. 12) protein sequences.

FIG. 11: Sequence of expressed rPAP (SEQ ID NO. 13), with internal disulfide bonding cysteines denoted in large bold type: Cys-34 binding to Cys-258 and Cys-84 binding to Cys-105; Bold; engineered linker with N-terminal cysteine; VNTI (residues 7-11 of SEQ ID NO. 13).: native PAP sequences; Bold and underlined is C-terminus of natural pre-PAP (post-translationally cleaved in the plant).

DETAILED DESCRIPTION

Figure 1:
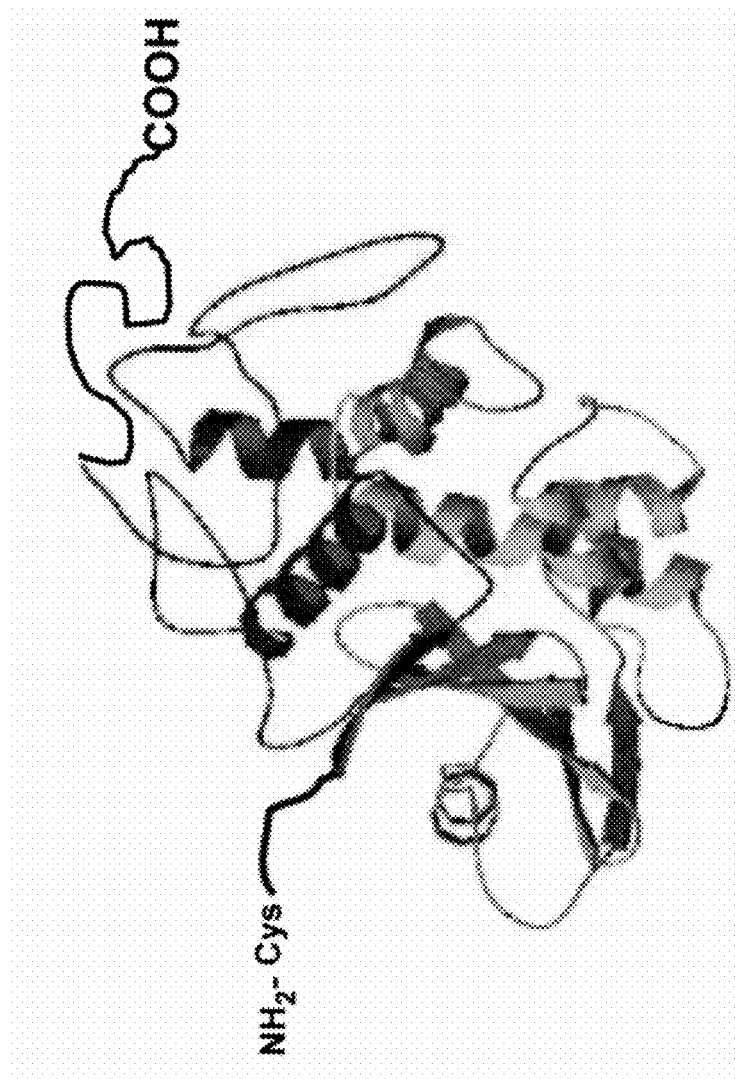
FIG. 1 is a stylized depiction of the structure of a full length pokeweed antiviral protein showing the C-terminal residues that are ordinarily cleaved in the plant during post translational processing, and additional, non-naturally-occurring, N-terminal amino acid residues.
Figure 2:
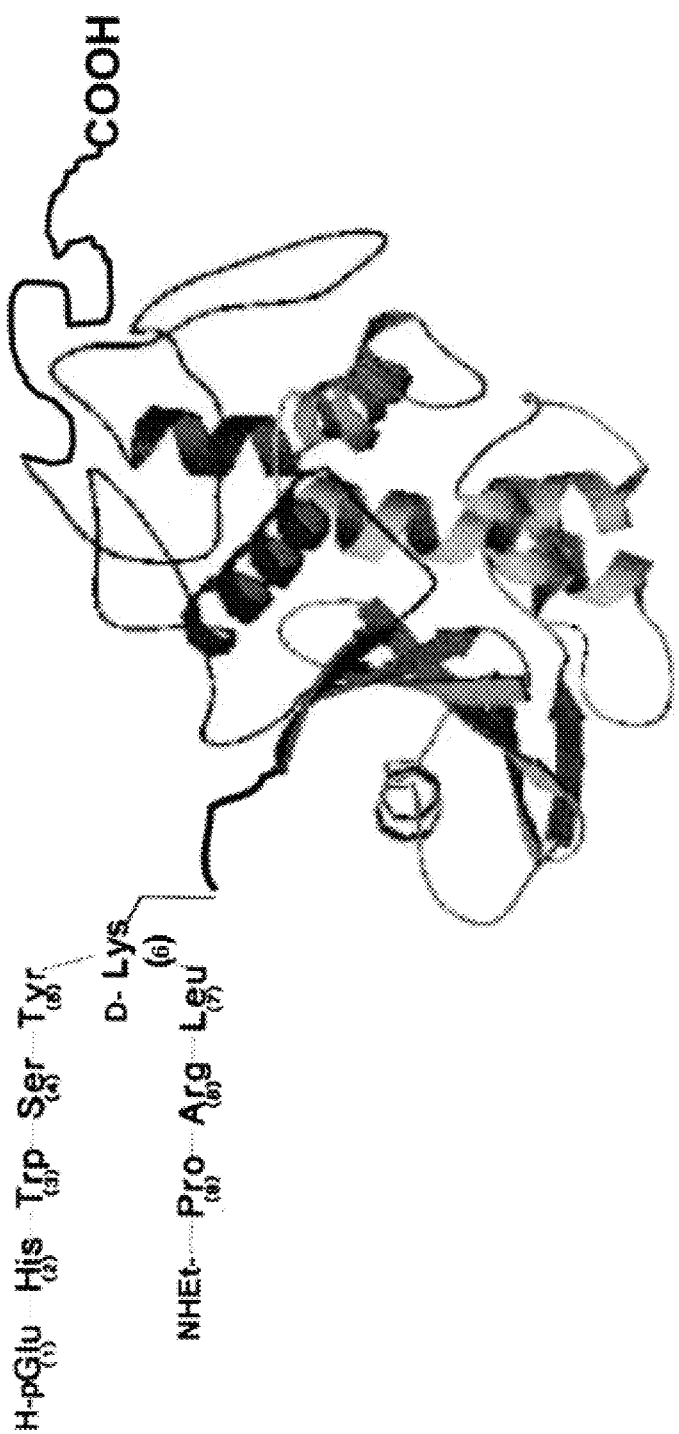
FIG. 2 is a stylized depiction of the structure of: a pokeweed antiviral protein showing C-terminal that are ordinarily cleaved in the plant during post translational processing; and additional, non-naturally-occurring, N-terminal amino acid residues; (SEQ ID NO. 7) a N-terminal linker; and an exemplary compound, modified gonadotropin releasing hormone (GnRH).
Figure 3:
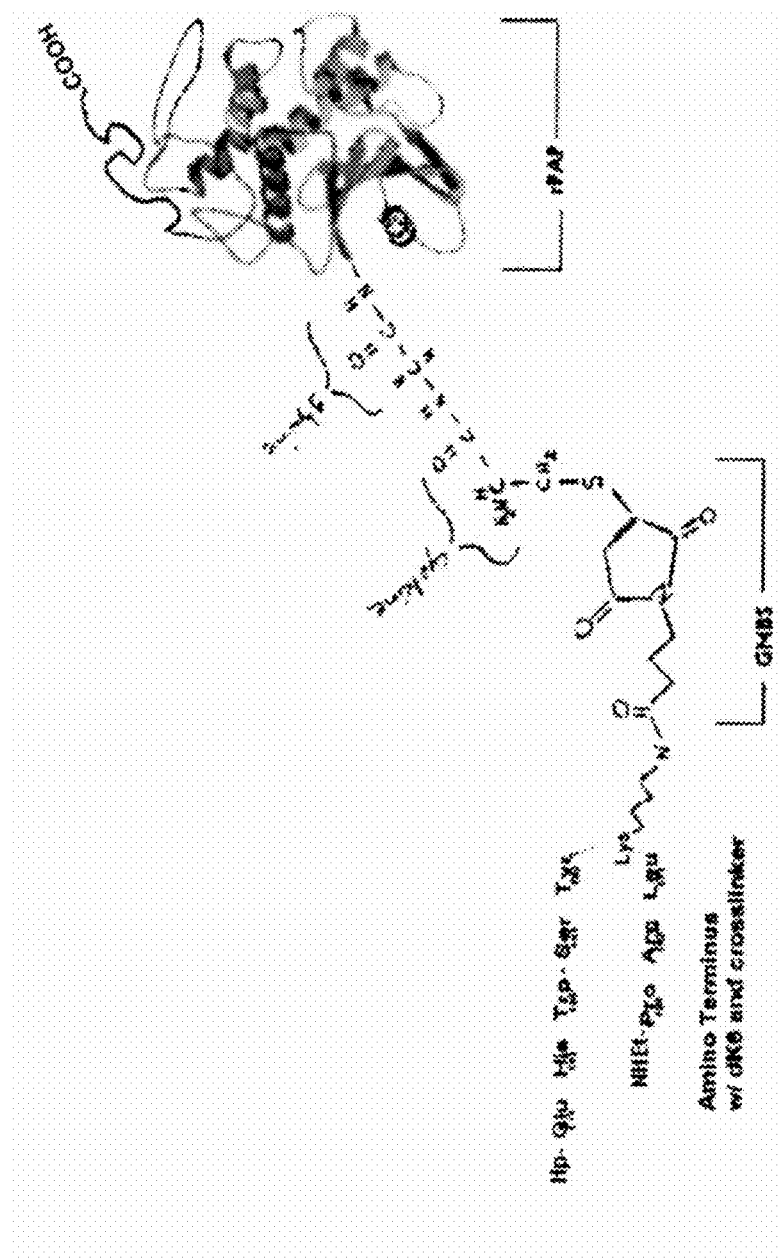
FIG. 3 is a stylized depiction of the structure of a recombinant non-cleavable (abbreviated "nc" and meaning that the linker does not possess a disulfide cleavage site) pokeweed conjugate, with detail at the amino terminus, including dK6 (SEQ ID NO. 7) and showing a linker and modified gonadotropin releasing hormone.
Figure 4:
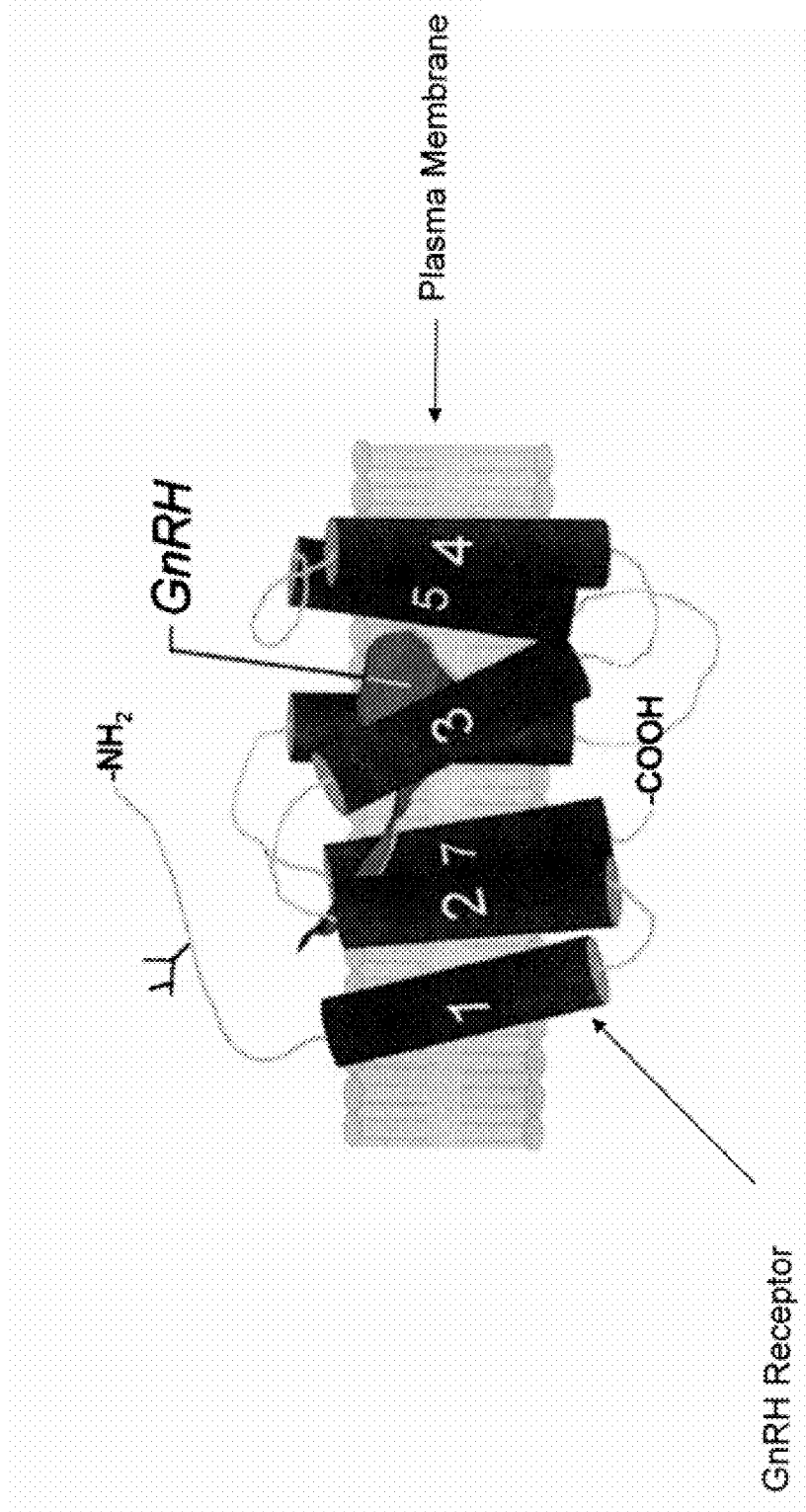
FIG. 4 is a stylized depiction of the interaction of gonadotropin releasing hormone and the extracellular domain of the gonadotropin releasing hormone receptor.

The present invention provides a recombinant pokeweed antiviral protein that is expressible at high yields in *E. coli*, and which has 30 to 40 times greater specific activity (biological activity/unit mass) than any other recombinant PAP. Moreover, the present invention provides methods for producing rPAP in pharmaceutical quantities.

The present rPAP materials (proteins, nucleic acids, constructs, cells, etc.) may be used to produce rPAP conjugates having rPAP and a targeting compound bound to them, either via a linker or directly. In one embodiment, the rPAP has a free cysteine, for optional use in linking a linker to another compound. In one such embodiment, the present rPAP proteins provide a convenient N-terminal cysteine for such purposes, although the use of the present rPAP is not limited to N-terminal conjugation. For instance, the rPAPs of the present invention may be used as a toxin without conjugation or may be conjugated via a free cysteine, at a terminal cysteine, or at an internal cysteine.

The rPAP molecules described herein are active in the rabbit reticulocyte lysate assay, with or without linker or targeting compounds conjugated to them.

The present invention includes methods to express, refold, conjugate and purify recombinant PAP. Several obstacles were overcome to achieve successful expression. The fundamental problem with expressing rPAP in non-pokeweed host cells is that it is a toxin and kills the host cells. Attempts were made to express the mature (post-translationally cleaved) PAP in E. coli, using the T7 system. The cells grew poorly, if at all, and showed distress prior to induction of the rPAP protein. Subsequently, attempts to express the full length rPAP (the mature PAP plus the C-terminal portion that is ordinarily cleaved post translationally in the plant) using the T7 inducible promoter system in E. coli were also unsuccessful. The cells also showed distress during the growth phase and prior to induction of the rPAP. Finally, the full length rPAP under two regulatory control signals was attempted in E. coli. The T7 RNA polymerase was put under the control of the arabinose (AraD) promoter, with the T7 promoter upstream of the full length rPAP sequence. With the arabinose promoter tightly suppressed, the cells were able to grow even while harboring the rPAP gene on a plasmid. Induction via removal of the suppression resulted in a pharmaceutically-workable yield of rPAP.

There are a variety of methods to refold the present rPAPs. The one that has been most successful is as described in Example 2. Another method is to use the protocol of Example 2, substituting using 0.5M L-arginine in place of sucrose. In addition, glutathione may be substituted for cysteamine in the Example 2 protocol. The inclusion bodies may optionally be solubilized with 6M guanidine-HCl instead of 8M urea. Refolding ideally is conducted in the basic pH range.

The protein may optionally be purified by a variety of methods including ion exchange chromatography, hydrophobic interaction chromatography, and hydroxyapetite chromatography, all of which are well-described in the art. The preferred method is cation exchange chromatography, particularly as described in Example 5.

Furthermore, based on experiments carried out on this recombinant protein, it was determined that the specific activity (biological activity/unit mass) of the inventive rPAPs are 30-40x more active in inhibiting protein translation in a rabbit reticulocyte lysate than another, reported, rPAP. The rPAP concentration was determined by rPAP-specific radioimmune assay, which is very sensitive, and can detect sub-nanomolar amounts of rPAP.

Recombinant PAP proteins, ideally folded so as to retain toxin function, preferably those retaining the natural disulfide bridges of the naturally-occurring cysteines, and preferably those having at least one free cysteine (eg. one that is not present in a naturally-occurring sequence), most preferably a terminal free cysteine capable of selectively binding other compounds, are provided herein. As is skill of the art, any PAP sequence is appropriate for use as a starting material in the present invention. Any known isotype, or any that becomes apparent will be useful for preparing the present invention.

Full length PAP has the following amino acid sequence at the C-terminus: YNQNAMFPQLIMSTYYNYVN-LGDLFEGF-COOH (SEQ ID NO. 6). This sequence is ordinarily cleaved in the pokeweed plant post-translationally but is retained in preferred embodiments of the present invention. Naturally-occurring, post-translationally-cleaved PAP has a molecular weight of 29,308.5 daltons.

In particular, rPAP compositions as described above, which are selected from the group consisting of SEQ ID NO. 1; a protein which comprises a free cysteine and is at least 90% identical to SEQ ID NO. 1 using the BLAST software version 2.2.21 on default settings; a protein which is encoded by SEQ ID NO. 2; a protein comprising a free cysteine and is encoded by a nucleic acid which is at least 90% identical to SEQ ID NO. 2 using BLAST version 2.2.21 software on default settings. However, also preferred are those compositions as above, wherein the sequence identity is selected from the group consisting of: 95%; 96%; 97%; 98%; and 99%.

Also provided are nucleic acids selected from the group consisting of: SEQ ID NO.2; a nucleic acid which is at least 85% identical to SEQ ID NO. 2 using the BLAST software version 2.2.21 on default settings and encodes a protein having a free cysteine; a nucleic acid which encodes SEQ ID NO.1; and a nucleic acid which encodes a protein having a free cysteine and is at least 85% identical to SEQ ID NO. 1 using BLAST software version 2.2.21 on default settings. However, also preferred are those compositions as above, wherein the sequence identity is selected from the group consisting of: 90%; 95%; 96%; 97%; 98%; and 99%. A preferred nucleic acid comprises a nucleic acid which encodes the proteins herein.

Also provided are methods to bind GMBS linker to d-lys6-gonadotropin releasing hormone, comprising incubating GMBS with d-lys6-gonadotropin releasing hormone under non-aqueous conditions. A more preferred embodiment of this method is one wherein said non-aqueous condition comprises the steps of: solubilizing GMBS in methanol to create a first non-aqueous solution; solubilizing d-lys6-gonadotropin releasing hormone in methanol to create a second non-aqueous solution; mixing said first and second non-aqueous solutions at a molar ratio of 1.1:1.

In particular, those rPAPs which are at least 90% identical, preferably at least 95% identical, most preferably at least 99% identical to SEQ ID NO. 1 are useful in the present methods. Those that also comprise a free CYS residue are most useful. Moreover, conserved sequences should not be changed, and non-conserved sequences are optionally changeable. In PAP, the disulfide bonds between naturally occurring cysteines provide the tertiary structure necessary for toxin function, and are ideally conserved in the present inventive molecules and methods. Mutations in the C-terminal domain affect processing localization of PAP, and may be altered if altered processing is desired. Mutations that affect RNA binding as well as depurination are known. For example, truncation of the first 16 amino acids eliminates PAP cytotoxicity and ability to depurinate ribosomes. In addition, ribosome depurination decreases as amino acids are removed from the C-terminus, and is eliminated when a stop codon is introduced at Glu-244. Moreover, hyperactive mutants can be screened by known methods, so as to obtain particularly toxic compounds. These mutational effects may be utilized so as to optimize function of the present invention. Moreover, these mutant rPAPs and compositions utilizing such mutants are within the scope of the present invention.

Nucleotides which, when expressed, result in a rPAP protein are also included in the present invention. In particular, SEQ ID NO. 2 is preferred. However, those in the art recognize that certain changes in the above sequence will not alter the fundamental aspects of the present invention. Therefore, the present invention includes nucleic acids which are homologous to using hybridization under stringent conditions, identical to using BLAST, have minor changes not affecting function, such as point mutations not changing the protein sequence, codon changes not changing the protein sequence, etc. with the nucleic acids of the present invention.

Also provided are conjugates and methods to conjugate a compound herein. Conjugates are ideally designed to selectively bind a receptor in which cell damage is desired. In general, after binding to the receptor via the targeting compound, the conjugate is taken up by receptor mediated endocytosis and delivers the conjugate to the cell. Following uptake, the rPAP portion of the conjugate binds to the ribosomal RNA by depurinating the conserved sarcin/ricin loop of the large ribosomal RNA. Depurinated ribosomes are unable to bind elongation factor 2, and, thus, the translocation step of the elongation cycle is inhibited, resulting in a shutdown of protein synthesis. The cell eventually dies.

One particular method for conjugating compounds to certain rPAP proteins herein comprises inducing a chemical bond between an N-terminal cysteine and another compound. Such methods, wherein the compound is an antibody, a hormone, a modified hormone releasing factor, or a hormone releasing factor are preferred. In particular, those wherein the hormone releasing factor is GnRH are more preferred, although most preferred is conjugation to a d-lys$_6$-modified GnRH. Conjugation can take place via any known method, but preferably via creation of a sulfhydryl bond between the targeting compound and the rPAP, whether via a linker or other bridging compound. In other words, taking advantage of a free cysteine, to the exclusion of binding to the other cysteines in the rPAP, is ideal, although those in the art are aware of ways to modify both the rPAP and the compound to which it is conjugated, so as to optimize the functionality.

In a preferred embodiment of the present invention, modified gonadotropin releasing hormone "d-lys$_6$-GnRH" is conjugated to full length rPAP. The d-lys$_6$-GnRH is preferably activated with the linker GMBS for ease of binding to a free cysteine on a full length rPAP. Such "activation" of the d-lys$_6$-GnRH with the GMBS proved an obstacle when attempted under aqueous conditions as would ordinarily be attempted. Under aqueous conditions, one d-lys$_6$-GnRH molecule was bound to 2-3 molecules of GMBS, which was unacceptable for binding one rPAP per d-lys$_6$-GnRH. However, when the d-lys$_6$-GnRH was activated under non-aqueous conditions (methanol), the obstacle was overcome: a ratio of one d-lys$_6$-GnRH to one GMBS linker molecule was achieved. Thus, a one-to-one ratio of rPAP to d-lys$_6$-GnRH was also achieved.

Those methods wherein a heterobifunctional crosslinker is utilized is preferred, particularly GMBS, but also any heterobifunctional crosslinker that will facilitate the binding to d-lys$_6$-GnRH via an NHS ester group located on the linker, or attachment to a free sulfhydryl group on the rPAP via a maleimide group located on the linker Both ends of the GnRH molecule are required for binding to the receptor. The only difference between GnRH and d-lys6-GnRH (also referred to interchangeably as "DK6" or "dK6" or "d-lys$_6$" or "d-Lys6") is the substitution at position 6 of a glycine for a D-lysine. In addition, the ends are blocked. The C-terminus is blocked with an ethyl-amide group (ET-NH$_2$), thereby replacing the glycine at position 10 of the natural compound. The natural GnRH compound is NH$_2$Glu-His-Trp-Ser-Tyr-Gly-Leu-Arg-Pro-GlyCOOH (SEQ ID NO. 7). The preferred analog is dK6: Hp-Glu-His-Trp-Ser-Tyr-DLys-Leu-Arg-Pro-Et-NH$_2$.

In another embodiment, amino acid sequence Cys-Gly-Gly-Gly-Gly-Ser (SEQ ID NO. 4) is added to the full length rPAP and used to bind targeting compound. Cys-Gly-Gly-Gly-Gly-Ser (SEQ ID NO. 4) is not part of the natural PAP sequence. Val-Asp are the first two amino acids of the natural PAP sequence.

A most preferred conjugate of the present invention has the following structure:

X-Y-Z wherein X is d-lys$_6$-GnRH; Y is a GMBS linker; and Z is a full length rPAP having CGGGGS (SEQ ID NO. 4) at the N-terminus.

Conjugates may be made via the methods described herein, or any method known or developed in the art. Moreover, conjugates may be modified so as to provide any functionality desired, as is known in the art. The examples describe the preferred conjugation methods.

Any salt, suspension, dispersion, etc. may be used so as to administer the present conjugates. Preferred is a 0.7%-10%, more preferably 0.9%, sodium chloride solution that is sterile and non-pyrogenic, more preferably such a solution that is also 4.5-7 pH. Moreover, any administration method is acceptable, provided that the conjugate provides the proper impact. The most preferred embodiment of the present invention is to use a rPAP-GNRH salt, in solution, to inject in animals, for the purpose of reproductive sterilization. Sterilization need not be complete, nor reversible; however, the best mode contemplated is a non-reversible rPAP-d-lys$_6$-GnRH injectible for use in animals, particularly dogs, cats, horses, livestock for food or other products (cattle, dairy cows, swine, sheep, goats, bison, bison/cattle breeds, etc.), working livestock, zoo animals, and wildlife (particularly deer, elk and other ungulates susceptible to chronic wasting disease).

The foregoing invention has been described in accordance with the relevant legal standards, thus the description is exemplary rather than limiting in nature. Variations and modifications to disclosed embodiments may become apparent to those skilled in the art and are within the scope of the invention.

EXAMPLES

Example 1

Expression of rPAP in *E. coli*

The full length sequence (SEQ ID NO. 2) was obtained by PCR amplification using a forward primer, rPAP-F: 5'-CCCGGG CATATG TGC GGA GGC GGA GGC AGT GTG AAT ACA ATC ATC TAC AAT GTT GGA AGT ACC-3 (SEQ ID NO.8), and a reverse primer, rPAP-R: 5'-GCG CGC AAG CTT TCA GGA TTC TTC AAA TAG ATC ACC AAG ATT AAC C (SEQ ID NO. 9).

The reaction mix consisted of the following components: 600 mM Tris-504 (pH 8.9), 180 mM Ammonium Sulfate, 0.2 mM dATP, 0.2 mM dCTP, 0.2 mM dGTP, 0.2 mM dTTP, 2 mM MgSO4, 0.2 µM rPAP-F primer, 0.2 µM rPAP-R primer, ing template DNA, 1 unit Platinum$^R$ Taq High Fidelity Polymerase (Invitrogen corp., Carlsbad, Calif.). The PCR reaction was carried out under the following conditions: 94° C.×2 min (1 cycle), 94° C.×30 sec, 52° C.×30 sec, 68° C.×1 min (15 cycles), 94° C.×30 sec, 55° C.×30 sec, 68° C.×1 min (25 cycles).

The full length sequence encoding rPAP was introduced (ligated) downstream of the T7 promoter in the pET3a expression plasmid using NdeI and BamHI (New England Biolabs, Ipswich, MA), according to manufacturer's instructions.

The rPAP sequence-containing plasmids were used to transform the One Shot® TOP10 Chemically Competent *E. coli* strain (Invitrogen Corporation, Carlsbad, Calif.). Several colonies were picked and screened by DNA sequence analysis for presence of the insert. The plasmid DNA from a colony that was shown to harbor the plasmid containing the correct rPAP sequences was purified and subsequently used to transform the BL21(AI) strain of *E. coli*, which possesses the T7 RNA polymerase under the control of the tightly regulated arabinose promoter (AraD), along with the ampicillin resistance selectable marker. The presumptive transformants were plated on LB selection medium and glucose, to select for transformants and suppress rPAP expression.

Two isolates were selected for study, and a control was generated which contained the expression plasmid without the rPAP sequence. Each isolate was separately grown approximately 12 hours (overnight) at 37° C., with shaking, in minimal media devoid of lactose and arabinose, and in the presence of glucose. The control was grown under the same conditions. The growth medium was selected for the purpose of repressing induction of the arabinose promoter system, thereby repressing rPAP RNA expression/protein translation.

The results were as follows:

|        | Isolate I A600 | Isolate II A600 | Control A600 |
|--------|----------------|-----------------|--------------|
| T0     | .06            | .07             | .060         |
| T1 hr  | .22            | .22             | .17          |
| T2 hr  | .44            | .50             | .48          |
| T2.3 hr| .68            | .73             | .69          |

A small amount of each overnight culture was transferred to LB media containing ampicillin, and after reaching an A600 of 0.4, rPAP was subsequently induced from the *E. coli* cells, by the addition of L-arabinose to a final concentration of 0.2%, and isopropyl β-D-1-thiogalactopyranoside to a concentration of 1 mM. Induction was carried out for a further 3.5 hr.

Example 2

Refolding and Purification of rPAP

The rPAP was refolded by snap dilution. Following isolation of the inclusion bodies, the inclusion bodies we solubilized in 8M urea, 50 mM Tris HCl, pH 8.5. DTT was added to a final concentration of 10 mM, and the mixture was stirred at room temperature for 90 min. The solubilized protein was than added dropwise into a solution containing 50 mM Tris, pH 8.5, 0.4M sucrose, 0.05% polyethylene glycol-3550, 0.9 mM oxidized cysteamine (TPEGS), while it was stirring at room temperature. The final concentration of rPAP in the refolding solution was between 10 µg/ml and 50 ug/ml. Following addition of the solubilized rPAP to the refold solution, the mixture was stirred for an additional 24 hours at 4° C. After 24 hours, the mixture was centrifuged at 16000×g for 15 min, the supernatant was decanted, and following refolding, the protein solution was dialyzed against buffer containing 50 mM Tris, pH 7.0, 1 mM EDTA. The pH of the buffer had a range of 6.8-8.5. After dialysis, the solution is centrifuged at 16000×g for 15 min., and the supernatant was placed over a cation exchange resin. The column is than washed with 50 mM Tris-HCl, pH 7.0, 1.0 mM EDTA, and the protein is eluted with a buffer containing 50 mM Tris, pH 7.0, 1M NaCl. The eluted protein is dialyzed against conjugation buffer, which contains 50 mM NaPO$_4$, pH 7.2, 100 mM NaCl, 1 mM EDTA. The protein concentration is adjusted to a concentration of 0.2 mg/ml-1.0mg/ml.

Example 3

Activation of d-lys$_6$ Modified Gonadotropin Releasing Hormone (GnRH) with maleimidobutyryloxy-succinimide ester (GMBS) Linker D-lys$_6$-GnRH, having a molecular weight of 1224 daltons, was prepared by solid-phase synthesis (Anaspec Corp., Fremont, Calif.). Six milligrams of d-lys$_6$-GnRH was mixed with 1.5 ml deionized methanol, and adjusted to a pH of 7.0 using diisopropylethanolamine (DIPEA).

GMBS was purchased from Thermo Fisher Scientific (Rockford, Ill.). 1.25 mg of GMBS was mixed with 1.5 ml deionized methanol.

1.5 ml of d-lys$_6$-GnRH-methanol and 1.5 ml of GMBS-methanol were mixed together in a capped serum bottle and adjusted to a pH 7.0, using DIPEA. The serum bottle was sealed using a metal cap. The solution was degassed, and purged with nitrogen four times. The serum bottle was covered with aluminum foil and the reaction was allowed to proceed, for 90 minutes, with stirring, at room temperature.

The resulting d-lys$_6$-GnRH-GMBS had a molecular weight of approximately 1421 daltons, indicating that one molecule of GMBS was bound to one molecule of d-lys$_6$-GnRH. This was confirmed by mass spectroscopy.

Example 4

Conjugation of rPAP to d-lys$_6$-GnrH-GMBS

The solution of Example 3 was evaporated with a centrifugal evaporation unit. TCEP.HCl Tris(2-Carboxyethyl)phosphine hydrochloride is added to a final concentration of 0.05 mM to the refolded recombinant PAP dissolved in conjugation buffer. The mixture was incubated for 1-2 hr at room temperature. After incubation, the refolded rPAP, dissolved in conjugation buffer, was added directly to the dried down d-lys$_6$-GnRH-GMBS so that the ration of d-lys$_6$-GnRH-GMBS to rPAP was 20:1. Tween 20 was added to a final concentration of 0.25%. The pH was adjusted to 7.3, if needed, using 10 mM phosphoric acid, and the reaction was allowed to proceed in the dark, at room temperature (70° F.) for approximately 2-3 hours.

Example 5

Purifying d-lys$_6$-GnRH-GMBS-rPAP

Following conjugation, d-lys$_6$-GnRH-GMBS-rPAP was further subjected to size exclusion chromatography using a 10 ml Bio-Rad Bio-Gel P10 column, to remove excess dK6 remaining after the conjugation reaction. The protein solution was dialyzed against buffer containing 50 mM Tris, pH 7.0, 1 mM EDTA. The pH of the buffer had a range of 6.8-8.5. Following dialysis, the solution was centrifuged at 16000×g for 15 min., and the supernatant was placed over a cation exchange resin. The column was than washed with the same buffer, and the protein was eluted with a buffer containing 50 mM Tris, pH 7.0, 1M NaCl.

Example 6

Receptor Binding Assay

The purified, refolded d-lys$_6$-GnRH-GMBS-rPAP of Example 5 was used in a competitive radio-immuno receptor binding assay. Purified pituitary membranes having gonadotropin releasing hormone receptors were flooded with I$^{125}$-radiolabeled d-Lys$_6$-GnRH. Different concentrations of the d-lys$_6$-GnRH-MBS-rPAP was subsequently added to the membranes, the membranes washed with 1 mM Tris-Cl Ph 7.4, 1 mM CaCl, 1% BSA. The reactions were incubated for 4 hr, diluted with the same buffer. Following dilution, the tubes were centrifuged at 16000×g for 15 min at 4° C., the tubes were decanted and the reduction in radioactivity measured. The same procedure was followed for a d-lys$_6$-GnRH-GMBS-plant-derived mature PAP. The concentrations are described in the table to this Example.

Figure 6:
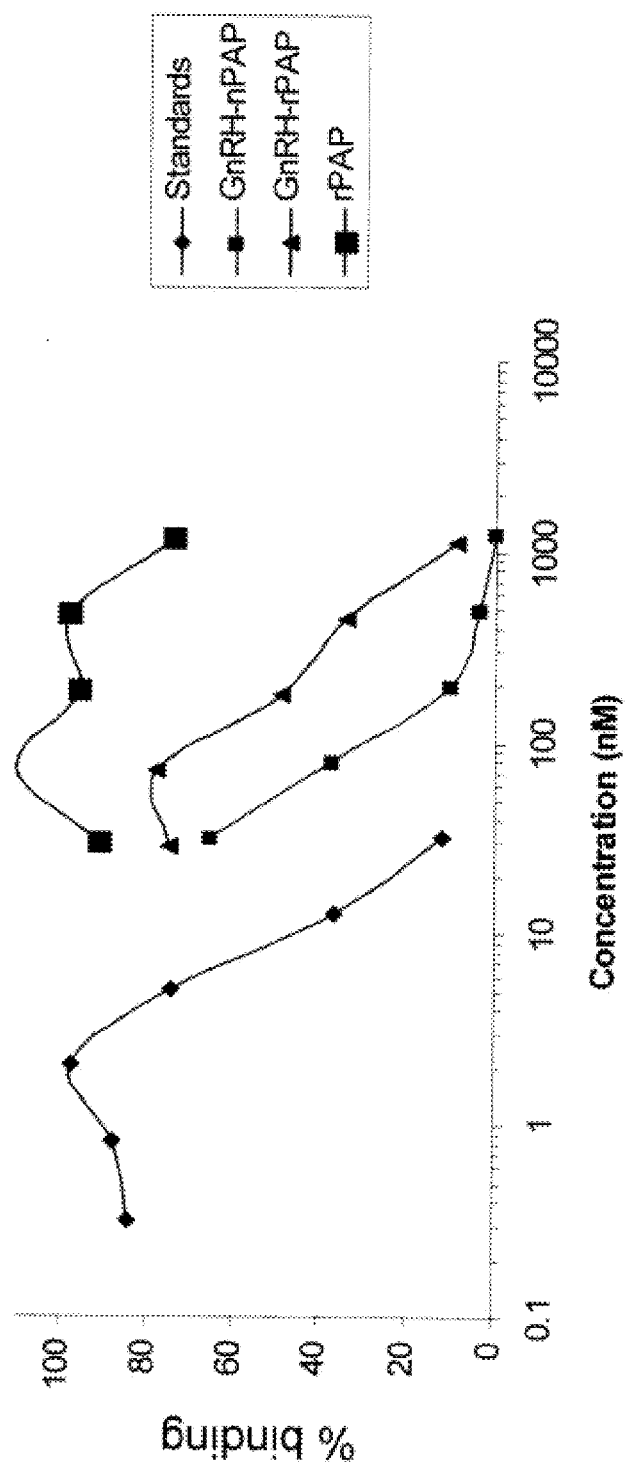
FIG. 6 is a graph depicting the results of a competitive radio-immuno receptor binding assay. The curve closest to the X axis reflects the data for the standards. The next curve reflects the data for a d-lys$_6$-GnRH-GMBS-PAP, wherein the PAP was purified from plant parts (also known as a natural or native PAP). The curve wherein the data points are depicted as triangles reflects the data for a d-lys$_6$-GnRH-GMBS-rPAP. The line wherein the data points are depicted as Xs reflects non-conjugated recombinant PAP (not bound to d-lys$_6$-GnRH-GMBS).

FIG. 6 depicts the results of this study. Both the native PAP-based conjugate and rPAP-based conjugate have an IC50 in the 70-200 nM range. The rPAP alone does not bind, and therefore does not show a concentration-dependant response.

Table for Example 6

| nM | Standards | nM | GnRH-rPAP | nM | GnRH-nPAP | nM | rPAP |
|---|---|---|---|---|---|---|---|
| 32 | 12.18 | 1102.94 | 9.24 | 1250 | 0.00 | 1136.36 | 74.75 |
| 12.8 | 36.67 | 441.18 | 34.04 | 500 | 3.38 | 454.55 | 98.71 |
| 5.12 | 74.26 | 176.47 | 49.42 | 200 | 10.05 | 181.82 | 96.36 |
| 2.048 | 97.57 | 70.59 | 78.20 | 80 | 37.53 | 72.73 | 110.76 |
| 0.819 | 88.00 | 28.24 | 75.05 | 32 | 65.53 | 29.09 | 91.50 |
| 0.32 | 84.12 | | | | | | |

Example 7

Rabbit Reticulocyte Lysate Assay

The following materials were used in this Example: Promega Flexi® Rabbit Reticulocyte Lysate System: L4540; Promega Luciferase Assay Reagent: L1483; Fischer Optizyme Recombinant RNAse Inhibitor: BP3222-5; Luminometer: Turner TD-20e. All buffers and solutions were prepared with DEPC-treated H2O. Dilution buffer was prepared [0.5 ml to 1 ml of a 0.5M stock (DEPC-treated H2O, 0.1M NaCl, dilution buffer (50 mM NaCl 0.5% Fraction V BSA)] for the toxins and/or toxin buffers to be tested.

The protocol was as follows:

First, a 0.5 nM dilution of the toxins/conjugates was prepared. Then, 100 uL serial dilutions (1:2.5 for each dilution) of the toxins/conjugates was prepared, using the 0.5 nM (500 pM) stock. The following dilutions were prepared: 200 pM; 80 pM; 32 pM; 12.8 pM; 5.12 pM.

To set up the assay, 2.5 uL DEPC-treated H$_2$O and 2.5 pL toxin/conjugate dilution was added to a sterile 0.65 ml eppindorf tube for each of the dilutions above, beginning with 500 pM.

The following following control reactions were also prepared: dilution buffer: positive control for RR lysate; 0.5 pM toxin/conjugate: high concentration positive control for toxin/conjugate activity.

The lysate was thawed on ice, and 17.5 uL of test dilution or control was added to each tube, on ice, and mixed gently with pipette. The lysate/test or control was then pre-incubated on ice for 15 min, and 2.5 ul of an nutrient premix was added after the 15 minute pre-incubation period (Amino acids (-lue); 4.2 uL; Amino acids (-met); 4.2 uL; 2.5M KCl 11.76 uL; RNAsin 8.4 uL; DEPC H$_2$O 10.92 uL; Luciferase mRNA 2.52 uL; total to 42 uL). During the 15 minute pre-incubation period, the mRNA is added to the pre-mix. The total volume of each reaction tube was 25 uL.

Figure 5:
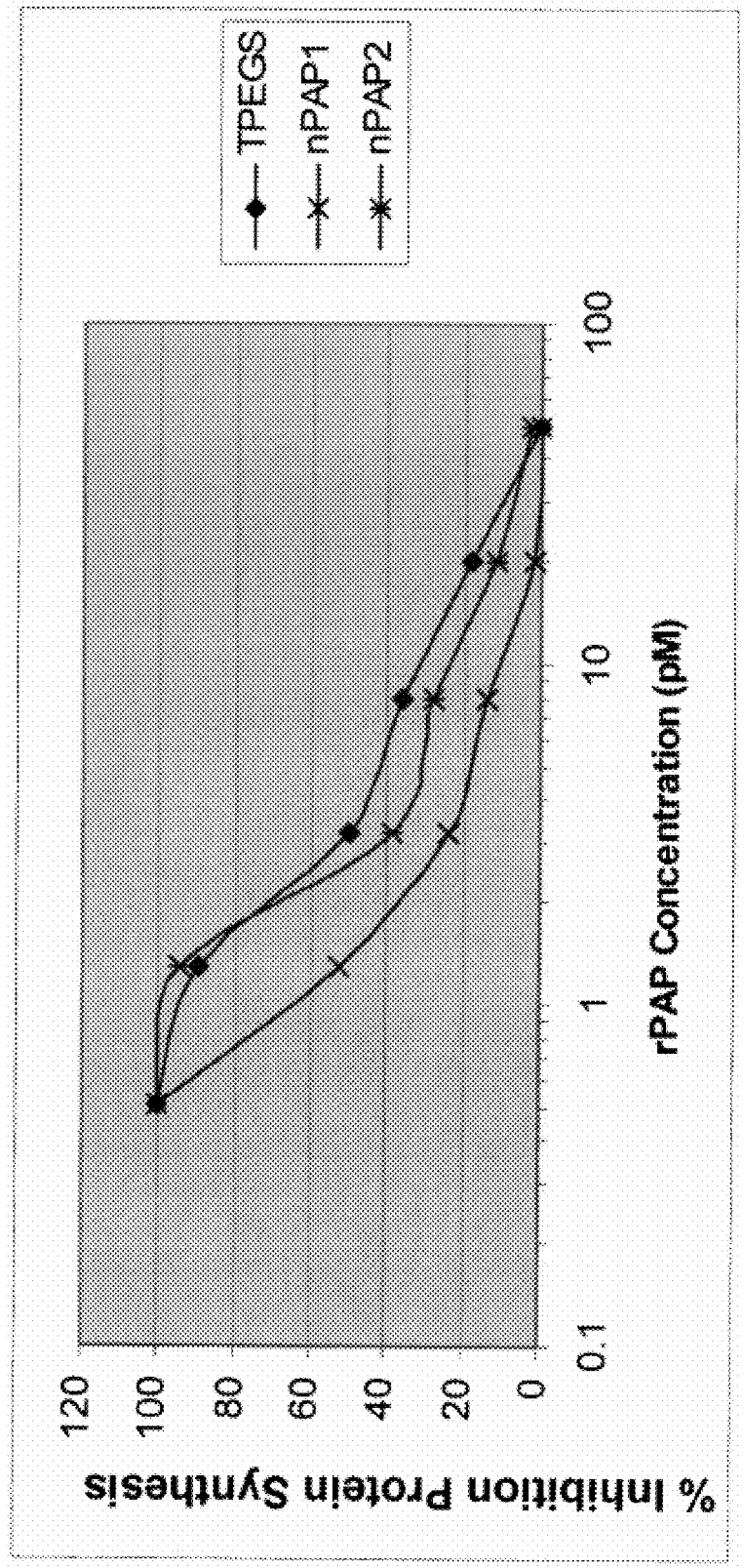
FIG. 5 is a graph depicting biological activity of rPAP as measured by inhibition of protein synthesis of a luciferase mRNA in rabbit reticulocyte lysate assay.

The contents of each reaction tube was mixed gently with a pipette and incubated in a 30° C. water bath for 90 minutes. An aliquot of 50 uL thawed, room temperature luciferase assay reagent (LAR) was transferred into luminometer tubes (in triplicate) and luL of reaction tube contents was added to a luminometer tube. The luminosity was counted in a luminometer. The log of concentration versus percentage of highest counts for each toxin/conjugate dilution series was plotted. The IC$_{50}$ was determined from the graph, for each sample. FIG. 5 is the graph produced from data, according to this Example.

Example 8

Toxicity of Mature rPAP to E. coli

In order to examine the biological activity of a recombinant form of PAP that has the same structure as the mature form of plant-derived mature PAP, the pET3a expression plasmid containing a T7 promoter upstream of one of four mature PAP-encoding sequences (each plasmid contains the DNA sequences encoding a mature form of rPAP that is identical to the post-translationally modified form of plant-derived PAP: clones 1-4.1, 1-4.2, 1-4.3, and 1-4.4) were transformed into *E. coli* BL21(AI) (Invitrogen Corp. Carlsbad, Calif.) having T7 RNA polymerase under control of an arabinose promoter (AraD). The cells were grown for approximately 12 hours (overnight) at 37° C. with shaking, in minimal media containing glucose and ampicillin The cells were transferred to Luria broth in the morning. The same process was followed for a full length clone (3.2). The cells harboring the plasmids were induced after growth for 2 hours by the addition of arabinose to a final concentration of 0.2%, and isopropyl β-D-1-thiogalactopyranoside to a concentration of 1 mM The A600 was measured every hour thereafter, for three hours. The results are shown in the table to Example 8.

Table to Example 8

| Clone | Innoculation | 1 hour | 2 hours | 3 hours |
|---|---|---|---|---|
| 1-4.1 | 0.100 | 0.052 | 0.022 | 0.038 |
| 1-4.2 | 0.107 | 0.041 | 0.026 | 0.032 |
| 1-4.3 | 0.099 | 0.052 | 0.090 | 0.037 |
| 1-4.4 | 0.094 | 0.045 | 0.067 | 0.087 |
| 3-2 (+) | 0.102 | 0.182 | 0.429 (induced) | 0.894 |
| 3.2 (−) | 0.094 | 0.221 | 0.474 | 1.147 |

Example 9

Toxicity of Full Length rPAP Under Certain Expression Conditions

A single colony from two different isolates and a control harboring plasmid without a rPAP insert were each inoculated into Luria broth medium containing 100 ug/ml ampicillan. The three cultures were then grown for approximately 18 hours (overnight) at 37° C., with shaking. Each grown culture was diluted 1:25 into fresh Luria broth medium, in the presence of 100 ug/ml ampicillan, and grown at 37° C., with shaking, for two hours.

The results were as follows:

| | Isolate I A600 | Isolate II A600 | Control A600 |
|---|---|---|---|
| T0 | .058 | .063 | .062 |
| T1 hr | .029 | .038 | .278 |
| T2 hr | .016 | .040 | .737 |

The invention claimed is:

1. A composition of matter comprising a recombinant pokeweed antiviral protein having an N-terminal cysteine.

2. A composition of claim 1, wherein said recombinant pokeweed antiviral protein is a full length recombinant pokeweed antiviral protein.

3. A composition of claim 2, which comprises Cys-Gly-Gly-Gly-Gly-Ser (SEQ ID NO:4) at the N-terminus of a full length recombinant pokeweed antiviral protein.

4. A nucleic acid comprising SEQ ID NO:2.

5. A plasmid comprising a nucleic acid of claim 4.

6. A cell comprising a nucleic acid of claim 5.

7. A cell of claim 6, which is *E. coli*.

* * * * *

SEQUENCE LISTING

<160> NUMBER OF SEQ ID NOS: 13

<210> SEQ ID NO 1
<211> LENGTH: 297
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Met Cys Gly Gly Gly Ser Val Asn Thr Ile Ile Tyr Asn Val Gly
1               5                   10                  15

Ser Thr Thr Ile Ser Lys Tyr Ala Thr Phe Leu Asn Asp Leu Arg Asn
            20                  25                  30

Glu Ala Lys Asp Pro Ser Leu Lys Cys Tyr Gly Ile Pro Met Leu Pro
        35                  40                  45

Asn Thr Asn Thr Asn Pro Lys Tyr Val Leu Val Glu Leu Gln Gly Ser
    50                  55                  60

Asn Lys Lys Thr Ile Thr Leu Met Leu Arg Arg Asn Asn Leu Tyr Val
65                  70                  75                  80

Met Gly Tyr Ser Asp Pro Phe Glu Thr Asn Lys Cys Arg Tyr His Ile
                85                  90                  95

Phe Asn Asp Ile Ser Gly Thr Glu Arg Gln Asp Val Glu Thr Thr Leu
            100                 105                 110

Cys Pro Asn Ala Asn Ser Arg Val Ser Lys Asn Ile Asn Phe Asp Ser
        115                 120                 125

Arg Tyr Pro Thr Leu Glu Ser Lys Ala Gly Val Lys Ser Arg Ser Gln
    130                 135                 140

Val Gln Leu Gly Ile Gln Ile Leu Asp Ser Asn Ile Gly Lys Ile Ser
145                 150                 155                 160

Gly Val Met Ser Phe Thr Glu Lys Thr Glu Ala Glu Phe Leu Leu Val
                165                 170                 175

Ala Ile Gln Met Val Ser Glu Ala Ala Arg Phe Lys Tyr Ile Glu Asn
            180                 185                 190

Gln Val Lys Thr Asn Phe Asn Arg Ala Phe Asn Pro Asn Pro Lys Val
        195                 200                 205

Leu Asn Leu Gln Glu Thr Trp Gly Lys Ile Ser Thr Ala Ile His Asp
    210                 215                 220

Ala Lys Asn Gly Val Leu Pro Lys Pro Leu Glu Leu Val Asp Ala Ser
225                 230                 235                 240

Gly Ala Lys Trp Ile Val Leu Arg Val Asp Glu Ile Lys Pro Asp Val
                245                 250                 255

Ala Leu Leu Asn Tyr Val Gly Gly Ser Cys Gln Thr Thr Tyr Asn Gln
            260                 265                 270
```

Asn Ala Met Phe Pro Gln Leu Ile Met Ser Thr Tyr Tyr Asn Tyr Val
            275                 280                 285

Asn Leu Gly Asp Leu Phe Glu Gly Phe
    290                 295

<210> SEQ ID NO 2
<211> LENGTH: 894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atgtgcggag gcggaggcag tgtgaataca atcatctaca atgttggaag taccaccatt      60
agcaaatacg ccacttttct gaatgatctt cgtaatgaag cgaaagatcc aagtttaaaa     120
tgctatggaa taccaatgct gcccaataca aatacaaatc aaagtacgt gttggttgag      180 ctccaaggtt caaataaaaa aaccatcaca ctaatgctga dacgaaacaa tttgtatgtg     240
atgggttatt ctgatccctt tgaaaccaat aaatgtcgtt accatatctt taatgatatc     300
tcaggtactg aacgccaaga tgtagagact actctttgcc caaatgccaa ttctcgtgtt     360
agtaaaaaca taaactttga tagtcgatat ccaacattgg aatcaaaagc gggagtaaaa     420
tcaagaagtc aggtccaact gggaattcaa atactcgaca gtaatattgg aaagatttct     480
ggagtgatgt cattcactga aaaaccgaa gccgaattcc tattggtagc catacaaatg      540
gtatcagagg cagcaagatt caagtacata gagaatcagg tgaaaactaa ttttaacaga     600
gcattcaacc ctaatcccaa agtacttaat ttgcaagaga catggggtaa gatttcaaca     660
gcaattcatg atgccaagaa tggagtttta cccaaacctc tcgagctagt ggatgccagt     720
ggtgccaagt ggatagtgtt gagagtggat gaaatcaagc ctgatgtagc actcttaaac     780
tacgttggtg ggagctgtca gacaacttat aaccaaaatg ccatgtttcc tcaacttata     840
atgtctactt attataatta catggttaat cttggtgatc tatttgaagg attc           894

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Ser
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Gly Gly Gly Gly Ser
1               5

```
<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Gly Gly Gly Gly Ser Gly Gly Gly Gly Ser
1               5                   10

<210> SEQ ID NO 6
<211> LENGTH: 28
<212> TYPE: PRT
<213> ORGANISM: Phytolacca americana

<400> SEQUENCE: 6

Tyr Asn Gln Asn Ala Met Phe Pro Gln Leu Ile Met Ser Thr Tyr Tyr
1               5                   10                  15

Asn Tyr Val Asn Leu Gly Asp Leu Phe Glu Gly Phe
            20                  25

<210> SEQ ID NO 7
<211> LENGTH: 10
<212> TYPE: PRT
<213> ORGANISM: Unknown
<220> FEATURE:
<223> OTHER INFORMATION: Description of Unknown: Gonadotropin releasing
      hormone peptide

<400> SEQUENCE: 7

Glu His Trp Ser Tyr Gly Leu Arg Pro Gly
1               5                   10

<210> SEQ ID NO 8
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cccgggcata tgtgcggagg cggaggcagt gtgaatacaa tcatctacaa tgttggaagt      60
acc                                                                   63

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcgcgcaagc tttcaggatt cttcaaatag atcaccaaga ttaacc                     46

<210> SEQ ID NO 10
<211> LENGTH: 897
<212> TYPE: DNA
<213> ORGANISM: Artificial Sequence
<220> FEATURE:
<223> OTHER INFORMATION: Description of Artificial Sequence: Synthetic
      polynucleotide
```

-continued

<400> SEQUENCE: 10

```
atgtgcggag gcggaggcag tgtgaataca atcatctaca atgttggaag taccaccatt      60
agcaaatacg ccactttttct gaatgatctt cgtaatgaag cgaaagatcc aagtttaaaa    120
tgctatggaa taccaatgct gcccaataca atacaaatc caaagtacgt gttggttgag     180
ctccaaggtt caaataaaaa aaccatcaca ctaatgctga gacgaaacaa tttgtatgtg    240
atgggttatt ctgatccctt tgaaaccaat aaatgtcgtt accatatctt taatgatatc    300
tcaggtactg aacgccaaga tgtagagact actctttgcc caaatgccaa ttctcgtgtt    360
agtaaaaaca taaactttga tagtcgatat ccaacattgg aatcaaaagc gggagtaaaa    420
tcaagaagtc aggtccaact gggaattcaa atactcgaca gtaatattgg aaagatttct    480
ggagtgatgt cattcactga aaaaccgaa gccgaattcc tattggtagc catacaaatg     540
gtatcagagg cagcaagatt caagtacata gagaatcagg tgaaaactaa ttttaacaga    600
gcattcaacc ctaatcccaa agtacttaat ttgcaagaga catggggtaa gatttcaaca    660
gcaattcatg atgccaagaa tggagtttta cccaaacctc tcgagctagt ggatgccagt    720
ggtgccaagt ggatagtgtt gagagtggat gaaatcaagc ctgatgtagc actcttaaac    780
tacgttggtg ggagctgtca gacaacttat aaccaaaatg ccatgttttcc tcaacttata   840
atgtctactt attataatta catggttaat cttggtgatc tatttgaagg attctga       897
```

<210> SEQ ID NO 11
<211> LENGTH: 785
<212> TYPE: DNA
<213> ORGANISM: Phytolacca americana

<400> SEQUENCE: 11

```
gtgaatacaa tcatctacaa tgttggaagt accaccatta gcaaatacgc cactttttctg     60
aatgatcttc gtaatgaagc gaaagatcca agtttaaaat gctatggaat accaatgctg    120
cccaatacaa atacaaatcc aaagtacgtg ttggttgagc tccaaggttc aaataaaaaa    180
accatcacac taatgctgag acgaaacaat ttgtatgtga tgggttattc tgatcccttt    240
gaaaccaata aatgtcgtta ccatatcttt aatgatatct caggtactga acgccaagat    300
gtagagacta ctctttgccc aaatgccaat tctcgtgtta gtaaaaacat aaactttgat    360
agtcgatatc caacattgga atcaaaagcg ggagtaaaat caagaagtca ggtccaactg    420
ggaattcaaa tactcgacag taatattgga aagatttctg gagtgatgtc attcactgag    480
aaaaccgaag ccgaattcct attggtagcc atacaaatgg tatcagaggc agcaagattc    540
aagtactaga gaatcaggtg aaaactaatt taacagagc attcaaccct aatcccaaag    600
tacttaattt gcaagagaca tggggtaaga tttcaacagc aattcatgat gccaagaatg    660
gagttttacc caaacctctc gagctagtgg atgccagtgg tgccaagtgg atagtgttga    720
gagtggatga atcaagcct gatgtagcac tcttaaacta cgttggtggg agctgtcaga    780
caact                                                                785
```

<210> SEQ ID NO 12
<211> LENGTH: 262
<212> TYPE: PRT
<213> ORGANISM: Phytolacca americana -continued

<400> SEQUENCE: 12

Val Asn Thr Ile Ile Tyr Asn Val Gly Ser Thr Thr Ile Ser Lys Tyr
1               5                   10                  15

Ala Thr Phe Leu Asn Asp Leu Arg Asn Glu Ala Lys Asp Pro Ser Leu
            20                  25                  30

Lys Cys Tyr Gly Ile Pro Met Leu Pro Asn Thr Asn Thr Asn Pro Lys
        35                  40                  45

Tyr Val Leu Val Glu Leu Gln Gly Ser Asn Lys Lys Thr Ile Thr Leu
    50                  55                  60

Met Leu Arg Arg Asn Asn Leu Tyr Val Met Gly Tyr Ser Asp Pro Phe
65                  70                  75                  80

Glu Thr Asn Lys Cys Arg Tyr His Ile Phe Asn Asp Ile Ser Gly Thr
                85                  90                  95

Glu Arg Gln Asp Val Glu Thr Thr Leu Cys Pro Asn Ala Asn Ser Arg
            100                 105                 110

Val Ser Lys Asn Ile Asn Phe Asp Ser Arg Tyr Pro Thr Leu Glu Ser
        115                 120                 125

Lys Ala Gly Val Lys Ser Arg Ser Gln Val Gln Leu Gly Ile Gln Ile
    130                 135                 140

Leu Asp Ser Asn Ile Gly Lys Ile Ser Gly Val Met Ser Phe Thr Glu
145                 150                 155                 160

Lys Thr Glu Ala Glu Phe Leu Leu Val Ala Ile Gln Met Val Ser Glu
                165                 170                 175

Ala Ala Arg Phe Lys Tyr Ile Glu Asn Gln Val Lys Thr Asn Phe Asn
            180                 185                 190

Arg Ala Phe Asn Pro Asn Pro Lys Val Leu Asn Leu Gln Glu Thr Trp
        195                 200                 205

Gly Lys Ile Ser Thr Ala Ile His Asp Ala Lys Asn Gly Val Leu Pro
    210                 215                 220

Lys Pro Leu Glu Leu Val Asp Ala Ser Gly Ala Lys Trp Ile Val Leu
225                 230                 235                 240

Arg Val Asp Glu Ile Lys Pro Asp Val Ala Leu Leu Asn Tyr Val Gly
                245                 250                 255

Gly Ser Cys Gln Thr Thr
            260

<210> SEQ ID NO 13
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Cys Gly Gly Gly Gly Ser Val Asn Thr Ile Ile Tyr Asn Val Gly Ser
1               5                   10                  15

Thr Thr Ile Ser Lys Tyr Ala Thr Phe Leu Asn Asp Leu Arg Asn Glu
            20                  25                  30

Ala Lys Asp Pro Ser Leu Lys Cys Tyr Gly Ile Pro Met Leu Pro Asn
        35                  40                  45

Thr Asn Thr Asn Pro Lys Tyr Val Leu Val Glu Leu Gln Gly Ser Asn
    50                  55                  60

Lys Lys Thr Ile Thr Leu Met Leu Arg Arg Asn Asn Leu Tyr Val Met
65                  70                  75                  80

-continued

```
Gly Tyr Ser Asp Pro Phe Glu Thr Asn Lys Cys Arg Tyr His Ile Phe
            85                  90                  95

Asn Asp Ile Ser Gly Thr Glu Arg Gln Asp Val Glu Thr Thr Leu Cys
           100                 105                 110

Pro Asn Ala Asn Ser Arg Val Ser Lys Asn Ile Asn Phe Asp Ser Arg
           115                 120                 125

Tyr Pro Thr Leu Glu Ser Lys Ala Gly Val Lys Ser Arg Ser Gln Val
           130                 135                 140

Gln Leu Gly Ile Gln Ile Leu Asp Ser Asn Ile Gly Lys Ile Ser Gly
145                 150                 155                 160

Val Met Ser Phe Thr Glu Lys Thr Glu Ala Glu Phe Leu Leu Val Ala
               165                 170                 175

Ile Gln Met Val Ser Glu Ala Ala Arg Phe Lys Tyr Ile Glu Asn Gln
               180                 185                 190

Val Lys Thr Asn Phe Asn Arg Ala Phe Asn Pro Asn Pro Lys Val Leu
               195                 200                 205

Asn Leu Gln Glu Thr Trp Gly Lys Ile Ser Thr Ala Ile His Asp Ala
           210                 215                 220

Lys Asn Gly Val Leu Pro Lys Pro Leu Glu Leu Val Asp Ala Ser Gly
225                 230                 235                 240

Ala Lys Trp Ile Val Leu Arg Val Asp Glu Ile Lys Pro Asp Val Ala
               245                 250                 255

Leu Leu Asn Tyr Val Gly Gly Ser Cys Gln Thr Thr Tyr Asn Gln Asn
               260                 265                 270

Ala Met Phe Pro Gln Leu Ile Met Ser Thr Tyr Tyr Asn Tyr Val Asn
           275                 280                 285

Leu Gly Asp Leu Phe Glu Gly Phe
290                 295
```